(12) United States Patent
Hite et al.

(10) Patent No.: US 8,506,936 B2
(45) Date of Patent: Aug. 13, 2013

(54) STABILIZED NICOTINE CHEWING GUM

(75) Inventors: W. Crawford Hite, Winchester, CA (US); Malini Batheja, Dix Hills, NY (US); Mohsen Sadatrezaei, Washington, NY (US)

(73) Assignee: Watson Laboratories, Inc., Copiague, NY (US)

( * ) Notice: Subject to any disclaimer, the term of this patent is extended or adjusted under 35 U.S.C. 154(b) by 418 days.

(21) Appl. No.: 12/277,590

(22) Filed: Nov. 25, 2008

(65) Prior Publication Data

US 2010/0130562 A1 May 27, 2010

(51) Int. Cl.
*A61K 9/58* (2006.01)
*A61P 25/34* (2006.01)
*A23G 4/06* (2006.01)
*A23G 4/12* (2006.01)

(52) U.S. Cl.
USPC .......... 424/48; 424/78.15; 424/751; 514/343

(58) Field of Classification Search
None
See application file for complete search history.

(56) References Cited

U.S. PATENT DOCUMENTS

| 3,877,468 | A | * | 4/1975 | Lichtneckert et al. ........ 131/359 |
| 4,277,562 | A | | 7/1981 | Modrovich |
| 4,641,667 | A | | 2/1987 | Schmekel et al. |
| 5,866,179 | A | | 2/1999 | Testa |
| 6,344,222 | B1 | * | 2/2002 | Cherukuri et al. ................ 426/6 |
| 7,241,805 | B2 | | 7/2007 | Oberegger et al. |
| 2004/0013767 | A1 | * | 1/2004 | Norman et al. .................. 426/5 |
| 2007/0160731 | A1 | | 7/2007 | Rathjen et al. |
| 2008/0131508 | A1 | | 6/2008 | Agarwal et al. |

FOREIGN PATENT DOCUMENTS

| WO | 2002102357 | 12/2002 |
| WO | 2005023227 | 3/2005 |

OTHER PUBLICATIONS

Remington, the science and practice of pharmacy, 21st Edition. Chapter 55, (pp. 1062-1063).*
Handbook of Functional Lipids, 2006, CRC Press, pp. 179 and 181.*
B.R. Copenheaver, International Search Report in PCT/US09/65728, Jan. 21, 2010, 3 pages, ISA/US, Alexandria, Virginia.
B. Giffo-Schmitt, International Preliminary Report on Patentability in PCT/US09/65728, May 31, 2011, International Bureau of WIPO, Geneva, Switzerland, 7 pages.
McNeil Products Ltd., Nicorette 2 mg Gum, Jan. 1, 2008.
C. Tardi, Supplementary European Search Report in EP 09832340.5, Apr. 17, 2012, Munich, Germany.

* cited by examiner

*Primary Examiner* — Frederick Krass
*Assistant Examiner* — Michael P Cohen
(74) *Attorney, Agent, or Firm* — Florek & Endres PLLC

(57) ABSTRACT

A nicotine chewing gum composition with improved stability.

10 Claims, No Drawings

STABILIZED NICOTINE CHEWING GUM

TECHNICAL FIELD OF THE INVENTION

The present invention relates to a stabilized chewing gum product that contains nicotine. In particular, the present invention relates to a nicotine chewing gum product that reduces or eliminates the use of liquid components that promote, facilitate and/or accelerate the oxidation of nicotine free base to nicotine-N-oxide.

BACKGROUND OF THE INVENTION

It has long been known that nicotine is a component of various tobacco products that contributes to addiction. The art is rich with methods for administering nicotine to humans without the use of tobacco. These tobacco-free nicotine administrations are designed to reduce human dependence on tobacco products. Some of the tobacco-free nicotine administration methods include transdermal patches or confectionary products such as lozenges. Another well-known method for administering nicotine without tobacco use is the use of chewing gum. Examples of nicotine chewing gums can be found in U.S. Pat. Nos. 3,845,217; 3,877,468; 3,901,248; 5,488,962 and 6,344,222 and Patent Cooperation Treaty Publication No. WO 2007/053096. Nicotine chewing gums are also commercially available under the trade names NICORETTE® and THRIVE®. These prior art nicotine chewing gums may be prepared with hydrophilic liquid plasticizers or solvents such as glycerin, propylene glycol, or ethanol. These hydrophilic liquids, even in small amounts, can promote the degradation of nicotine to undesirable impurities.

Nicotine, or 3-(1-methyl-2-pyrrolidinyl)pyridine, is a tertiary amine with the following structure:

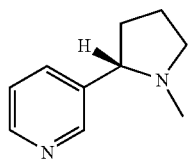

Under ambient conditions, nicotine is an oily, volatile, hygroscopic liquid that is sensitive to light and air. Nicotine's chemical and physical properties present a number of processing and stability issues. For example, because nicotine is volatile, it may evaporate during its incorporation into an administration vehicle such as a gum or lozenge. In addition, the nitrogen in the pyrrolidinic ring can undergo protonation in the presence of an acid. Nicotine free base is labile to oxidation through an electrophilic attack.

Some of the components that may be used in nicotine gums contain non-bonded electron pairs which tend to promote and/or facilitate the unwanted oxidation of the nicotine free base present in nicotine chewing gum. When the ingredients with non-bonded electron pairs are in liquid form, even in relatively small concentrations, the pyrrolidinic nitrogen in the nicotine molecule is more prone to oxidation and unwanted degradation.

In an effort to reduce the processing and stability issues associated with the nicotine compound, a number of nicotine complexes have been described in the art. For example, U.S. Pat. No. 5,512,306 employs a complex of cyclodextrin and nicotine to prepare smoking substitutes such as tablets and powders. A more common method involves the preparation of a complex of nicotine and an ion exchange resin. Nicotine ion exchange complexes are described in U.S. Pat. Nos. 3,845,217; 3,877,468; and 3,901,468, which are incorporated herein by reference. A well-known complex that is currently used in the commercially-available nicotine chewing gums is nicotine polacrilex which is a complex of nicotine and the cation exchange resin AMBERLITE 164.

Although the aforementioned nicotine complexes have improved the processing and stability of nicotine, they have not completely solved the problems. For example, these complexes retain some nicotine free base. The residual nicotine free base is prone to oxidation especially when in the presence of liquids with non-bonded electron pairs, especially liquids with hydroxide moieties.

It is therefore an object of the present invention to provide a nicotine-containing chewing gum having improved stability.

It is a further object of the present invention to provide a nicotine containing chewing gum that has a longer shelf life than the currently available nicotine chewing gums.

It is also an object of the present invention to provide a nicotine containing chewing gum that exhibits reduced levels of trans-Nicotine-N-oxide and cis-Nicotine-N-Oxide upon storage.

It is an additional object of the present invention to provide a nicotine chewing gum that is prepared without a liquid that contains non-bonded electron pairs, preferably without liquids that contain hydroxyl moieties.

It is also an additional object of the present invention to provide a nicotine containing chewing gum that is prepared with only hydrophobic liquids.

It is another object of the present invention to provide a nicotine containing chewing gum that is prepared with little or no hydrophilic liquids.

These and other objects of the present invention will become apparent from a review of the appended specification.

SUMMARY OF THE INVENTION

The foregoing objectives and others are obtained by preparing a nicotine chewing gum without a liquid that contains non-bonded electron pairs, preferably without a liquid that contains hydroxide moieties. In one embodiment of the invention, the nicotine chewing gum is prepared without a hydrophilic liquid. In an alternate embodiment of the invention, the nicotine chewing gum is prepared with only hydrophobic liquids.

It is known that protonated nicotine which exists as a complex with a cation exchange resin is not reactive to oxidation, and, therefore, the nicotine in the cation exchange resin complex is stable. However, the nicotine cation exchange resin complex contains a small portion of nicotine free base. Any chemical compound existing in the microenvironment of the nicotine free base that can share non-bonding electron pairs with the nicotine free base will promote, i.e., facilitate and/or accelerate, the production of unwanted nicotine-N-oxide compound. For example, it is believed that liquids such as water and ethanol which contain hydroxyl functional groups can easily invade the microenvironments containing nicotine free base and promote the oxidation to nicotine-N-oxide. The nicotine-N-oxide can occur in the cis or trans configuration, with the trans being more stable and, therefore, more prominent.

In order to reduce and/or avoid the potential oxidation reaction at the positively charged pyrrolidinic nitrogen of the nicotine molecule, the present invention is a nicotine chewing gum that is substantially free of liquids containing moieties with non-bonded electron pairs that promote the oxidation of nicotine free base. The nicotine chewing gum in accordance with the present invention should contain or be prepared with about 0% to about 1% by weight based upon the total weight of the nicotine chewing gum, of a liquid that contains non-bonded electron pairs which promote the oxidation of nicotine free base, preferably about 0% to about 0.5% by weight of the total weight of the nicotine chewing gum, and most preferably about 0% to about 0.25% by weight of the total weight of the nicotine chewing gum. If possible, the nicotine chewing gum prepared in accordance with the present invention will be prepared without any liquid that contains non-bonded electron pairs that promote the oxidation of nicotine free base.

In one embodiment of the present invention, the nicotine chewing gum is substantially free of liquids containing hydroxyl moieties that can easily invade the microenvironments of the nicotine free base in the nicotine chewing gum. The nicotine chewing gum in accordance with this embodiment should contain or be prepared with about 0% to about 1% by weight based upon the total weight of the nicotine chewing gum of a liquid that contains hydroxyl moieties, preferably about 0% to about 0.5% by weight of the total weight of the nicotine chewing gum, and most preferably about 0% to about 0.25% by weight of the total weight of the nicotine chewing gum. If possible, the nicotine chewing gum prepared in accordance with this embodiment will be prepared without any liquid that contains hydroxyl moieties.

Another embodiment of the present invention is a nicotine chewing gum that is substantially free of hydrophilic liquids. This embodiment of the present invention should contain or be prepared with about 0% to about 1% by weight based upon the total weight of the nicotine chewing gum of a hydrophilic liquid, preferably about 0% to about 0.5% by weight of the total weight of the nicotine chewing gum and most preferably about 0% to about 0.25% by weight of the total weight of the nicotine chewing gum. Ideally, the nicotine chewing gum prepared in accordance with this embodiment of the present invention should be prepared without any hydrophilic liquid and, therefore, will not contain a hydrophilic liquid. Some examples of hydrophilic liquids that have been used in the preparation of nicotine chewing gums include plasticizers, solvents and flavor carriers. Specific examples of the hydrophilic liquids that have been used in gums, but are not used in the present invention, include, but are not limited to, water, triacetin, propylene glycol polyethylene glycol, glycerin, and ethanol. These hydrophilic liquids all possess non-bonded electron pairs and/or hydroxyl moieties that are believed to promote the unwanted oxidation of nicotine free base.

A further embodiment of the present invention is a nicotine chewing gum free or substantially free of hydrophilic liquids as described above but that contains hydrophobic liquids. The preferred hydrophobic liquids should be free or substantially free of hydroxyl moieties and if possible free or substantially free of liquids that contain non-bonded electron pairs which promote the oxidation of nicotine free base to nicotine-N-oxide. It is believed the use of hydrophobic liquids improve the stability of the nicotine in the chewing gum by reducing the premature release of nicotine free base from the nicotine resin complexes and by making a hostile environment for oxidative reactions to occur. It is further believed the hostile environment may be created by the hydrophobic liquid forming a microenvironment around the positively charged pyrrolidine nitrogen atom of the nicotine molecules. The presence of the hydrophobic liquid may also reduce the hygroscopic characteristic of the nicotine during processing and storage of the nicotine gum. Examples of the hydrophobic liquids that may be used in the present invention include, but are not limited to, triglycerides, vegetable oils, lecithin and mixtures thereof. These hydrophobic liquids may be employed in the nicotine gum as plasticizers or flavor carriers.

In yet another embodiment of the present invention, the nicotine chewing gum is free or substantially free of any liquid that contains non-bonded electron pairs that promote the oxidation of nicotine free base as described above, free or substantially free of any liquid that contains hydroxyl moieties as described above, free or substantially free of any hydrophilic liquid as described above and only contains a hydrophobic liquid as described above.

DETAILED DESCRIPTION OF THE INVENTION

The present invention is a stabilized nicotine-containing chewing gum. The nicotine present in the chewing gum can be any of the well known forms of nicotine such as a base, salt or a nicotine complex. Nicotine salts can include nicotine hydrogen tartrate, nicotine bitartrate, nicotine hydrochloride, nicotine dihydrochloride, nicotine sulfate, nicotine citrate, nicotine zinc chloride monohydrate and nicotine salicylate. The nicotine complex may be a regenerative adsorbent complex as described in U.S. Pat. No. 3,877,468, a cyclodextrin complex as described in U.S. Pat. No. 5,512,306 or ion exchange complexes as described in U.S. Pat. Nos. 3,845,217 and 3,901,248. The preferred form of nicotine is a nicotine cation ion exchange complex such as a complex prepared with a cation exchange resin such as AMBERLITE 164. The nicotine-AMBERLITE 164 complex is commonly known as nicotine polacrilex. Unless otherwise specified, the term "nicotine" as used herein encompasses all of the aforementioned forms of nicotine, and especially nicotine cation exchange resin complexes.

The amount of nicotine present in the individual chewing gum units can range from about 0.01 weight percent to about 10 weight percent based upon the total weight of the individual chewing gum unit, preferably about 0.5 weight percent to about 5 weight percent and most preferably about 0.5 weight percent to about 4 weight percent. Typically, each chewing gum unit should contain about 1 mg to about 10 mg, preferably about 2 mg to about 5 mg of nicotine. It should be understood by an individual of ordinary skill that the aforementioned milligram amounts are base upon the amount of nicotine free base present in the chewing gum. More specifically, if the nicotine is present in the individual chewing gum units in the form of a salt or ion complex, an individual of ordinary skill should be able to determine the amount of nicotine salt or complex to add to the chewing gum formulation so the individual units contain between 1 mg and 10 mg of nicotine free base.

The chewing gum base used in the present invention can be any type of conventional gum base. The gum base can be a natural or synthetic product. Examples of natural gum bases include Chicle-, Jelutong-, Lechi di Caspi-, Soh-, Siak-, Katiau-, Sorwa-, Balata-, Pendare-, Perillo-, Malaya-, and Percha-gums, natural caoutchouc such as Crepe, Latex, and Sheets and natural resins such as Dammar and Mastix. Examples of synthetic gum bases include polyvinylacetate ("Vinnapas"), "Dreyco" commercial gum base, polyvinyl esters, polyisobutylene and non-toxic butadiene-styrene lattices. Examples of the chewing gum bases are provided in U.S. Pat. Nos. 3,877,468; 6,344,222 and 6,627,234, which are incorporated herein by reference.

The present invention may also include additional ingredients to improve or modify the organoleptic properties of the chewing gum. Some examples of the additional ingredients include plasticizers, buffering agents, sweeteners, flavoring agents, fillers, coloring agents and mixtures of the foregoing. These additional additives should be free of any liquid that contains non-bonded electron pairs that promote the oxidation of nicotine free base, preferably free of any hydroxyl moieties, hydrophilic liquid and, if necessary, should employ a hydrophobic liquid. If the additional additives do contain non-bonded electron pairs, the additive should be hydrophobic and/or employ a structure wherein the non-bonded electron pairs are sterically hindered in such as way as to hinder the non-bonded electron pairs from approaching the microenvironment of the nitrogen atom of the pyrrolidinic ring of the nicotine molecules.

Plasticizers, which are sometimes referred to as and may include softeners and emulsifiers in the chewing gum art, can be added to the present invention to reduce the viscosity of the gum base to a favorable or desirable consistency. Examples include lecithin, lanolin, glycerides (mono- and di-), stearic acid, sodium stearate, potassium stearate, glycerol triacetate (aka triacetin), glycerol monostearate and mixtures of the foregoing. Waxes such as beeswax, microcrystalline wax, rice bran wax, polyethylene wax, petroleum wax, paraffin, carnauba wax, candilla wax, cocoa butter and degreased cocoa powder may also be used as plasticizers in the present invention. Additional plasticizers that may be used in the present invention can include oils such as completely or partially hydrogenated vegetable oils, hydrogenated cotton seed oil, hydrogenated coconut oil, mineral oil and olive oil. Animal fats may also be used as plasticizers in the present invention. Combinations of any of the above plasticizers may also be used in the present invention. The plasticizer should comprise about 0.05% to about 30% by weight of the chewing gum final composition, preferably about 0.1% to about 20% based upon the final weight of the composition.

Examples of buffering agents that can be used in the present invention include conventional buffering agents such as calcium hydroxide, magnesium hydroxide, aluminum hydroxide and carbonate and phosphate salts such as sodium carbonate, potassium carbonate, calcium carbonate, sodium bicarbonate, potassium bicarbonate trisodium phosphate and calcium hydroxide. Mixtures of the foregoing may also be employed in the present invention. One embodiment of the present invention will include the amount of buffering agent present in the chewing gum sufficient to increase the pH of the saliva to around 7.0 or higher, preferably 7.5 or higher, and most preferably about 8-10 for about 3-12 minutes, preferably about 5-10 minutes from the time the chewing gum unit is placed in the mouth and the chewing process begins. The increase and maintenance of the saliva pH is beneficial because it reduces the throat irritating sensation created by the release of the nicotine from the chewing gum. The buffering agent should be present in an amount of about 0.1 to about 10% of the final composition, preferably about 0.5% to about 7.5% base upon the final weight of the chewing gum composition, and most preferably about 1% to about 5% based upon the final weight chewing gum composition.

Some of the buffering agents mentioned above may contain non-bonded electron pairs that theoretically could promote the unwanted oxidation reaction with the nicotine molecules. It is believed that the use of solid materials such as the aforementioned buffering agents with non-bonded electron pairs will not promote the unwanted oxidation of the nicotine molecules when used in the present invention because the solid compounds will not adequately penetrate the microenvironment of the nitrogen atom of the pyrrolidinic ring of the nicotine molecules.

Examples of sweeteners that may be used in the present invention include saccharide materials such as mono-, di-, tri- and polysaccharides as well as oligosaccharides. Sugars such as sucrose, glucose (corn syrup), dextrose, invert sugar, fructose and lactose may be used. Sugar free or non-sucrose formulations can include saccharin and its various salts such as sodium saccharin and calcium saccharin, and/or cyclamic acid and it various salts. Dipeptide sweeteners, chlorinated sugar derivatives, sucralose, dihydrochalcone, glycyrrhin, Stevia rebaudiana (Stevioside) and sugar alcohols such as sorbitol, mannitiol, xylitol, hexa-resorcinal may also be used in the present invention. Additional sweeteners that may be used in the present invention include aspartame, acesulfame potassium, thaumatin, maltodextrin and polydextrose. A more complete list of sweeteners can be found in U.S. Pat. Nos. 6,344,222 and 5,487,902, which are incorporated herein by reference. The sweetener should comprise about 5 to about 75% of the final chewing gum composition, preferably about 10 to about 60% and most preferably about 15% to about 45% of the final composition. The sweeteners should be free of any liquid that contains non-bonded electron pairs that promote the oxidation of nicotine free base, preferably be free of any hydroxyl moieties, hydrophilic liquid and, if necessary, should employ a hydrophobic liquid. If the sweetener does contain non-bonded electrons pairs, the sweetener should be a solid when added to the chewing gum composition, a hydrophobic material and/or employ a structure wherein the non-bonded electron pairs are sterically hindered in such as way as to inhibit the non-bonded electron pairs from approaching the microenvironment of the nitrogen atom of the pyrrolidinic ring of the nicotine molecules.

Flavoring agents that can be used in the present invention include peppermint, spearmint, wintergreen, cinnamon, coconut, coffee, chocolate, vanilla, menthol, liquirice, anise, apricot, caramel, pineapple, strawberry, raspberry, grape, cherry, mixed berry, tropical fruits, mint and mixtures thereof. The flavoring agent should comprise about 0.01% to about 5% of the final chewing gum composition, preferably about 0.1% to about 3% based upon the final chewing gum composition. Many of the conventional and commercially available flavoring agents employ a liquid carrier. When selecting an appropriate flavoring agent, care should be taken to insure the carrier is free of any liquid that employs non-bonded electron pairs that promote the oxidation of nicotine free base. In particular, the carrier for the flavoring agent should be free of hydroxyl moieties and should not be a hydrophilic liquid. It is preferred that the carrier for the flavoring agent be a hydrophobic liquid.

The present invention may also comprise a filler. Examples of possible fillers include calcium carbonate, talc, sodium sulfate, aluminum oxide, magnesium carbonate, kaolin, silicon dioxide, calcium phosphate or mixtures of the foregoing. The filler should be a solid material, preferably without non-bonded electron pairs that promote the oxidation of nicotine free base, hydrophobic and/or should employ a structure wherein the non-bonded electron pairs are sterically hindered in such as way as to inhibit the non-bonded electron pairs from approaching the microenvironment of the nitrogen atom of the pyrrolidinic ring of the nicotine molecules.

The present invention may also comprise a coloring agent to improve the color and appearance of the final composition. Examples of coloring agents include FD&C-type dyes and lakes, fruit and vegetable extracts, titanium dioxide and mixtures of the foregoing. It is preferred that the coloring agent be a solid material, more preferably without the presence of non-bonded electron pairs, hydrophobic and/or should employ a structure wherein the non-bonded electron pairs are sterically hindered in such as way as to inhibit the non-bonded electron pairs from approaching the microenvironment of the nitrogen atom of the pyrrolidinic ring of the nicotine molecules. If the coloring agent employs a liquid carrier care should be taken to insure the carrier is free of any liquid that employs non-bonded electron pairs that promote the oxidation of nicotine free base. In particular, the carrier for the coloring agent should be free of hydroxyl moieties and should not be a hydrophilic liquid. It is preferred that the carrier for the coloring agent be a hydrophobic liquid. If the carrier for the coloring agent is a hydrophilic liquid or contains a hydroxyl moiety, the amount of the coloring agent carrier should be kept to a minimum, preferably less than 0.1% of the chewing gum composition and more preferably less than 0.05% of the chewing gum composition.

In general, the present invention is prepared by adding the various ingredients to a commercially available mixer and mixing the ingredients until a homogeneous mixture is obtained. The homogeneous mixture is discharged from the mixer and shaped into the desired forms such as rolling sheets and cutting into sticks, extruding into chunks or casting into pellets which may be optionally coated with an aesthetic coating or seal coating and packaged into plastic bottles or foil sealed blister packages.

In one embodiment, the ingredients are mixed by first melting the gum base and adding it to a running mixer or melting the gum base in a mixer and adding the remaining ingredients such as the nicotine, sweetener, flavors and buffers to the melted gum base. The entire mixing procedure can range from 10 to 180 minutes and may depend upon the ingredients employed, batch size and the sequence in which they are combined. The amounts, durations and sequence of mixing are all within the ability of an individual of ordinary skill in the art.

After shaping the final chewing gum unit, it may optionally be coated with an aesthetic coating prior to packaging. A possible aesthetic coating is described in U.S. Pat. No. 6,627,234, which is incorporated herein by reference.

The present invention is stable for more than two years and is preferably shelf stable after packaging for at least three years. In one embodiment of the present invention, the nicotine chewing gum should contain no more than 6% of the trans nicotine-N-oxide, preferably no more than 5% of the trans nicotine-N-oxide, and most preferably no more than 4% of the trans nicotine-N-oxide when placed in a sealed HDPE bottle and stored for four (4) weeks at 50° C. and 75% relative humidity. The present invention should also contain no more than 4% of the cis nicotine-N-oxide, preferably no more than 3% of the cis nicotine-N-oxide, and most preferably no more than 2.5% of the cis nicotine-N-oxide when placed in a sealed HDPE bottle and stored for four (4) weeks at 50° C. and 75% relative humidity.

In another embodiment of the present invention, the nicotine chewing gum should contain no more than 6% of the trans nicotine-N-oxide, preferably no more than 5% of the trans nicotine-N-oxide, and most preferably no more than 4% of the trans nicotine-N-oxide when placed in a foil backed blister package and stored for six (6) months at 40° C. and 75% relative humidity. The present invention should also contain no more than 3% of the cis nicotine-N-oxide, preferably no more than 2.5% of the cis nicotine-N-oxide, and most preferably no more than 2% of the cis nicotine-N-oxide when placed in a foil backed blister package and stored for six (6) months at 50° C. and 75% relative humidity. This embodiment should also contain the following amounts of the trans and cis forms of the nicotine-N-oxide after one month, two months and three months of storage at 40° C. and 75% relative humidity:

|  | Preferred | More Preferred | Most Preferred |
|---|---|---|---|
| One Month |  |  |  |
| Trans Nicotine-N-Oxide | NMT 2.0% | NMT 1.5% | NMT 1.0% |
| Cis Nicotine-N-Oxide | NMT 1.0% | NMT 0.75% | NMT 0.5% |
| Two Months |  |  |  |
| Trans Nicotine-N-Oxide | NMT 3.0% | NMT 2.0% | NMT 1.5% |
| Cis Nicotine-N-Oxide | NMT 1.5% | NMT 1.0% | NMT 0.75% |
| Three Months |  |  |  |
| Trans Nicotine-N-Oxide | NMT 4.0% | NMT 2.5% | NMT 2.0% |
| Cis Nicotine-N-Oxide | NMT 2.0% | NMT 1.5% | NMT 1.0% |

(NMT = not more than)

The above amounts of the trans and cis isomers of nicotine-N-oxide are analyzed by high performance liquid chromatography using a YMC PACK PRO C18, 5 μm, 150 mm×4.6 mm column. The mobile phase consists of 180 ml methanol, 120 ml acetonitrile, 3.63 g sodium decylsulfonate, 5.44 sodium acetate trihydrate and 3 ml acetic acid in 700 ml of water. A flow rate of 1.0 ml/min, column temperature of 30° C., injection volume of 10 μl and a run time of 25 minutes was used. The degradation products were eluted at relative retention time for cis-nicotine-1'-N-oxide: 0.4 and trans-nicotine-1'-N-oxide: 0.7. Chromatograms were recorded by UV detector at 254 nm.

The test sample is prepared by weighing and transferring a portion of the chewing gum equivalent to a piece of chewing gum containing 4 mg of nicotine into a 250 ml Erlenmeyer flask. 100 ml of 0.2 N HCl is added to the flask followed by 100 ml of 90:10 mixture of hexane:methylene chloride. The contents of the flask are stirred for about 30 minutes or until the chewing gum sample is dispersed. The phases are allowed to separate until a clear lower layer is obtained. The clear lower layer is filtered through a SUPELCO C18 Environmental SPE ENVI solid extraction filter washed with 5 ml of methanol and 5 ml of 0.2 N HCl prior to filtering. The filtrate is collected in an HPLC vial for analysis as described above.

DESCRIPTION OF THE PREFERRED EMBODIMENTS

The following is provided as an example and is not intended to be limiting.

Example 1

A 4 mg nicotine chewing gum unit in accordance with the present invention was prepared with the following composition:

| Ingredient | Percent | mg/unit |
|---|---|---|
| Nicotine Polacrilex (18%) | 2.55 | 24.44 |
| DREYCO Gum Base | 67.99 | 652.74 |
| Sorbitol | 22.1 | 212.16 |
| Fruit Mint Flavor | 3.8 | 36.50 |
| Sodium Carbonate | 2.00 | 19.2 |
| Sodium Bicarbonate | 1.00 | 9.6 |
| Acesulfame Potassium | 0.25 | 2.4 |
| L-Methanol | 0.25 | 2.4 |
| D&C Yellow 10 and Brown Lakes | 0.05 | 0.4 |

The above composition was prepared by adding 1359.7 g of DREYCO gum base to a jacketed high shear mixer. The gum base was heated to about 60° C. and 50.9 g of nicotine polacrilex, 442 g of sorbitol, 76 g of fruit mint flavor with tri-glyceride as a carrier, 40 g of sodium carbonate, 20 g of sodium bicarbonate, 5.0 g of acesulfame potassium, 5.0 g of L-menthol and 0.8 g of D&C Yellow #10 lake were added.

After the ingredients were mixed, the mixture was cooled to approximately 38° C. and removed from the mixer and then rolling and scoring processes were performed to produce individual gum pieces. The gums then packaged into high density polyethylene bottles that were sealed and capped. The bottles were stored at 50° C. and 75% relative humidity for 4 weeks. The stored chewing gum was periodically tested for degradation by HPLC. The results of this testing are reported in Table 1.

Comparative Example 1

A 4 mg nicotine chewing gum unit not in accordance with the present invention was prepared with the following composition:

| Ingredient | Percent | mg/unit |
|---|---|---|
| Nicotine Polacrilex (18%) | 2.55 | 24.44 |
| DREYCO Gum Base | 67.99 | 652.74 |
| Sorbitol | 22.1 | 212.16 |
| Fruit Mint Flavor | 3.8 | 36.50 |
| Sodium Carbonate | 2.00 | 19.2 |
| Sodium Bicarbonate | 1.00 | 9.6 |
| Acesulfame Potassium | 0.25 | 2.4 |
| L-Methanol | 0.25 | 2.4 |
| D&C Yellow 10 and Brown Lakes | 0.05 | 0.4 |

The above composition was prepared by adding 1359.7 g of DREYCO gum base to a jacketed high shear mixer. The gum base was heated to about 60° C. and 50.9 g of nicotine polacrilex, 442 g of sorbitol, 76 g of fruit mint flavor with Ethanol as a carrier, 40 g of sodium carbonate, 20 g of sodium bicarbonate, 5.0 g of acesulfame potassium, 5.0 g of L-menthol and 0.8 g of D&C Yellow #10 lake were added.

After the ingredients were mixed, the mixture was cooled to approximately 38° C. and removed from the mixer and then rolling and scoring process were performed to produce individual gum pieces. The gums then packaged into high density polyethylene bottles that were sealed and capped. The bottles were stored at 50° C. and 75% relative humidity for 4 weeks. The stored chewing gum was periodically tested for degradation by HPLC. The results of this testing are reported in Table 1.

Comparative Example 2

A 4 mg nicotine chewing gum unit not in accordance with the present invention was prepared with the following composition:

| Ingredient | Percent | mg/unit |
|---|---|---|
| Nicotine Polacrilex (18%) | 2.55 | 24.44 |
| DREYCO Gum Base | 67.99 | 652.74 |
| Sorbitol | 2.1 | 212.16 |
| Fruit Mint Flavor | 3.8 | 36.50 |
| Sodium Carbonate | 2.00 | 19.2 |
| Sodium Bicarbonate | 1.00 | 9.6 |
| Acesulfame Potassium | 0.25 | 2.4 |
| L-Methanol | 0.25 | 2.4 |
| D&C Yellow 10 and Brown Lakes | 0.05 | 0.4 |

The above composition was prepared by adding 1359.7 g of DREYCO gum base to a jacketed high shear mixer. The gum base was heated to about 60° C. and 50.9 g of nicotine polacrilex, 442 g of sorbitol, 76 g of fruit mint flavor with propylene glycol as a carrier, 40 g of sodium carbonate, 20 g of sodium bicarbonate, 5.0 g of acesulfame potassium, 5.0 g of L-menthol and 0.8 g of D&C Yellow #10 lake were added.

After the ingredients were mixed, the mixture was cooled to approximately 38° C. and removed from the mixer and then rolling and scoring process were performed to produce individual gum pieces. The gums then packaged into high density polyethylene bottles that were sealed and capped. The bottles were stored at 50° C. and 75% relative humidity for 4 weeks. The stored chewing gum was periodically tested for degradation by HPLC. The results of this testing are reported in Table 1.

TABLE 1

| | Trans* | Cis** | Cotinine | Nornicotine |
|---|---|---|---|---|
| Example 1 | | | | |
| Initial | None Detected | None Detected | <0.1% | None Detected |
| 1 week | 1% | 0.6% | <0.1% | <0.1% |
| 2 weeks | 1.6% | 0.9% | <0.1% | None Detected |
| 4 weeks | 3.7% | 2% | <0.1% | None Detected |
| Comparative Example 1 | | | | |
| Initial | None Detected | None Detected | <0.1% | None Detected |
| 1 week | 2.2% | 1.1% | <0.1% | None Detected |
| 2 weeks | 2.8% | 1.5% | <0.1% | None Detected |
| 4 weeks | 6.5% | 3.2% | 0.1% | None Detected |
| Comparative Example 2 | | | | |
| initial | None Detected | None Detected | <0.1% | None Detected |
| 1 week | 2.3% | 1.2% | <0.1% | None Detected |
| 2 weeks | 3.4% | 1.7% | <0.1% | None Detected |
| 4 weeks | 7.3% | 3.5% | <0.1% | None Detected |

*= trans nicotine-N-oxide
**= cis nicotine-N-oxide.

The data reported in Table 1 shows that nicotine chewing gum prepared in accordance with the present invention exhibits an improved stability profile over the prior art nicotine chewing gum compositions that contain hydrophilic liquids.

The data reported in Table 1 was obtained by high performance liquid chromatography using a YMC PACK PRO C18, 5 µm, 150 mm×4.6 mm column. The mobile phase consists of 180 ml methanol, 120 ml acetonitrile, 3.63 g sodium decylsulfonate, 5.44 sodium acetate trihydrate and 3 ml acetic acid in 700 ml of water. A flow rate of 1.0 ml/min, column temperature of 30° C., injection volume of 10 µl and a run time of 25 minutes was used. The degradation products were eluted at relative retention time for cis-nicotine-1'-N-oxide: 0.4 and trans-nicotine-1'-N-oxide: 0.7. Chromatograms were recorded by UV detector at 254 nm.

The test sample was prepared by weighing and transferring a portion of the chewing gum equivalent to a piece of chewing gum containing 4 mg of nicotine into a 250 ml Erlenmeyer flask. 100 ml of 0.2 N HCl was added to the flask followed by 100 ml of 90:10 mixture of hexane:methylene chloride. The contents of the flask were stirred for about 30 minutes or until the chewing gum sample was dispersed. The phases were allowed to separate until a clear lower layer was obtained. The clear lower layer was filtered through a SUPELCO C18 Environmental SPE ENVI solid extraction filter, washed with 5 ml of methanol and 5 ml of 0.2 N HCl prior to filtering. The filtrate was collected in an HPLC vial for analysis as described above.

Example 2

A 4 mg nicotine chewing gum unit in accordance with the present invention was prepared with the following composition:

| Ingredient | Percent | mg/unit |
|---|---|---|
| Nicotine Polacrilex (18%) | 2.55 | 24.44 |
| DREYCO Gum Base | 67.09 | 644.1 |
| Sorbitol | 23.2 | 222.72 |
| Fruit Mint Flavor | 3.6 | 34.56 |
| Sodium Carbonate | 2.00 | 19.2 |
| Sodium Bicarbonate | 1.00 | 9.6 |
| Acesulfame Potassium | 0.25 | 2.4 |
| L-Methanol | 0.25 | 2.4 |
| Yellow and Brown Lakes | 0.05 | 0.4 |

The above composition is prepared by adding 610.6 kg of DREYCO gum base to a jacketed high shear mixer. The gum base is heated to about 60° C. and 23.5 kg of nicotine polacrilex, 210.7 kg of sorbitol, 32.8 kg of fruit mint flavor with tri-glyceride as a carrier, 18.2 kg of sodium carbonate, 9.1 kg of sodium bicarbonate, 2.3 kg of acesulfame potassium, 2.3 kg of L-menthol and 0.5 kg of Color lakes were added.

After the ingredients were mixed, the mixture was cooled to approximately 38° C. and removed from the mixer and then rolled and scored. Individual gum pieces then packaged into conventional foil backed blister packing. The blister packs were stored at 40° C. and 75% relative humidity for six months. The stored chewing gum was periodically tested by high performance liquid chromatography for degradation. The results of this testing are reported in Table 2.

Comparative Example 3

A 4 mg nicotine chewing gum unit in accordance with the present invention was prepared with the following composition:

| Ingredient | Percent | mg/unit |
|---|---|---|
| Nicotine Polacrilex (18%) | 2.55 | 24.44 |
| DREYCO Gum Base | 67.09 | 644.1 |
| Sorbitol | 23.2 | 222.72 |
| Fruit Mint Flavor | 3.6 | 34.56 |
| Sodium Carbonate | 2.00 | 19.2 |
| Sodium Bicarbonate | 1.00 | 9.6 |
| Acesulfame Potassium | 0.25 | 2.4 |
| L-Methanol | 0.25 | 2.4 |
| Yellow and Brown Lakes | 0.05 | 0.4 |

The above composition is prepared by adding 610.6 kg of DREYCO gum base to a jacketed high shear mixer. The gum base is heated to about 60° C. and 23.5 kg of nicotine polacrilex, 210.7 kg of sorbitol, 32.8 kg of fruit mint flavor with propylene glycol and Ethanol as a carrier, 18.2 kg of sodium carbonate, 9.1 kg of sodium bicarbonate, 2.3 kg of acesulfame potassium, 2.3 kg of L-menthol and 0.5 kg of Color lakes were added.

After the ingredients were mixed, the mixture was cooled to approximately 38° C. and removed from the mixer and then rolled and scored. Individual gum pieces then packaged into conventional foil backed blister packing. The blister packs were stored at 40° C. and 75% relative humidity for six months. The stored chewing gum was periodically tested by high performance liquid chromatography for degradation. The results of this testing are reported in Table 2.

TABLE 2

| | Assay | Trans Nicotine-N-oxide | Cis Nicotine-N-oxide | Total Impurities (excluding Trans-Nicotine-N-oxide) |
|---|---|---|---|---|
| Example 2 | | | | |
| 1 month | 107.0% | 0.5% | 0.2% | 0.2% |
| 2 months | 104.8% | 0.7% | 0.4% | 0.4% |
| 3 months | 103.5% | 1.1% | 0.5% | 0.5% |
| 6 months | 100.1% | 2.5% | 1.2% | 1.2% |
| Comparative Example 3 | | | | |
| 1 month | 102.8% | 2.2% | 1.1% | 1.1% |
| 2 months | 99.2% | 3.3% | 1.7% | 1.7% |
| 3 months | 98.8% | 4.4% | 2.1% | 2.1% |
| 6 months | 94.7% | 8.6% | 4.0% | 4.0% |

The data reported in Table 2 shows the nicotine chewing gum prepared in accordance with the present invention exhibits a much slower growth of the trans and cisisomers of nicotine-N-oxide than the nicotine chewing gum that employs hydrophilic liquids.

The data reported in Table 2 was obtained by high performance liquid chromatography using a YMC PACK PRO C18, 5 μm, 150 mm×4.6 mm column. The mobile phase consists of 180 ml methanol, 120 ml acetonitrile, 3.63 g sodium decylsulfonate, 5.44 sodium acetate trihydrate and 3 ml acetic acid in 700 ml of water. A flow rate of 1.0 ml/min, column temperature of 30° C., injection volume of 10 μl and a run time of 25 minutes was used. The degradation products were eluted at relative retention time for cis-nicotine-1'-N-oxide: 0.4 and trans-nicotine-1'-N-oxide: 0.7. Chromatograms were recorded by UV detector at 254 nm.

The test sample was prepared by weighing and transferring a portion of the chewing gum equivalent to a piece of chewing gum containing 4 mg of nicotine into a 250 ml Erlenmeyer flask. 100 ml of 0.2 N HCl was added to the flask followed by 100 ml of 90:10 mixture of hexane:methylene chloride. The contents of the flask were stirred for about 30 minutes or until the chewing gum sample was dispersed. The phases were allowed to separate until a clear lower layer was obtained. The clear lower layer was filtered through a SUPELCO C18 Environmental SPE ENVI solid extraction filter, washed with 5 ml of methanol and 5 ml of 0.2 N HCl prior to filtering. The filtrate was collected in an HPLC vial for analysis as described above.

While certain preferred and alternative embodiments of the invention have been set forth for purposes of disclosing the invention, modifications to the disclosed embodiments may occur to those who are skilled in the art. Accordingly, this specification is intended to cover all embodiments of the invention and modifications thereof which do not depart from the spirit and scope of the invention.

We claim:

1. A stable chewing gum composition comprising nicotine, a chewing gum base and a flavoring agent in a liquid carrier wherein the liquid carrier for the flavoring agent is a triglyceride and the chewing gum composition contains 0% to about 0.5% by weight based upon the total weight of the chewing gum composition of a liquid containing hydroxyl moieties that promote oxidation of nicotine free base; and wherein the chewing gum composition contains no more than 6% of trans nicotine-N-oxide and no more than 4% of cis nicotine-N- oxide when placed in a sealed plastic bottle and stored for four (4) weeks at 50° C. and 75% relative humidity.

2. The stable chewing gum composition as defined in claim 1 wherein the chewing gum composition is free of any liquid containing hydroxyl moieties that promote oxidation of nicotine free base.

3. The stable chewing gum composition as defined in claim 1 further comprising an organoleptic additive selected from the group consisting of a plasticizer, a buffering agent, a sweetener, a filler, a coloring agent and mixtures of the foregoing.

4. The stable chewing gum composition as defined in claim 1 that contains no more than 5% of the trans nicotine-N-oxide and no more than 3% of the cis nicotine-N-oxide.

5. The stable chewing gum composition as defined in claim 1 that contains no more than 4% of the trans nicotine-N-oxide and no more than 2.5% of the cis nicotine-N-oxide.

6. The stable chewing gum composition as defined in claim 1 that contains no more than 6% of the trans nicotine-N-oxide and no more than 3% of the cis nicotine-N-oxide when packaged in a foil backed blister package and stored for six months at 40° C. and 75% relative humidity.

7. The stable chewing gum composition as defined in claim 6 that contains no more than 5% of the trans nicotine-N-oxide and no more than 2.5% of the cis nicotine-N-oxide.

8. The stable chewing gum composition as defined in claim 6 that contains no more than 4% of the trans nicotine-N-oxide and no more than 2.0% of the cis nicotine-N-oxide.

9. A stable chewing gum composition as defined in claim 1 wherein the chewing gum composition comprises 0% to about 0.25% by weight based upon the total weight of the chewing gum composition of a liquid containing hydroxyl moieties.

10. A stable chewing gum composition comprising:
(a) Nicotine polacrilex;
(b) a chewing gum base;
(c) a flavoring agent in a hydrophobic liquid carrier wherein the hydrophobic liquid carrier is a triglyceride; and
(d) an organoleptic additive selected from the group consisting of a plasticizer, a buffering agent, a sweetener, a filler, a coloring agent and mixtures of the foregoing and wherein:
the chewing gum composition comprises 0% to about 0.5% by weight based upon the total weight of the chewing gum composition of a liquid containing hydroxyl moieties;
the chewing gum composition contains no more than 5% of the trans nicotine-N-oxide and no more than 3% of the cis nicotine-N-oxide when placed in a sealed plastic bottle and stored for four (4) weeks at 50° C. and 75% relative humidity; and
the chewing gum composition contains no more than 5% of the trans nicotine-N-oxide and no more than 2.5% of the cis nicotine-N-oxide when packaged in a foil backed blister package and stored for six months at 40° C. and 75% relative humidity.

* * * * *